United States Patent
DeWindt et al.

(10) Patent No.: US 7,276,055 B2
(45) Date of Patent: Oct. 2, 2007

(54) OVAL-SHAPED CARDIAC CANNULA

(75) Inventors: David B. DeWindt, Grand Rapids, MI (US); Ronald A. Devries, Zeeland, MI (US); Steven R. Gundry, Redlands, CA (US); William E. Sidor, Rockford, MI (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/407,094

(22) Filed: Apr. 3, 2003

(65) Prior Publication Data

US 2003/0191447 A1    Oct. 9, 2003

Related U.S. Application Data

(63) Continuation of application No. 10/026,234, filed on Dec. 21, 2001, now Pat. No. 6,645,194, which is a continuation of application No. 09/012,520, filed on Jan. 23, 1998, now Pat. No. 6,447,484, which is a continuation-in-part of application No. 08/780,995, filed on Jan. 9, 1997, now Pat. No. 5,817,071.

(51) Int. Cl.
*A61M 31/00* (2006.01)

(52) U.S. Cl. .................. 604/506; 604/206; 604/264

(58) Field of Classification Search ............... 604/4.01, 604/43, 28, 500, 506–508, 93.01, 96.01, 604/97.01–97.03, 98.01, 164.11, 99.01–99.04, 604/102.01–102.03, 103, 104, 158, 164.02, 604/167.01, 167.02, 167.04, 167.06, 170.02, 604/264, 323; 128/207.15
See application file for complete search history.

(56) References Cited

U.S. PATENT DOCUMENTS

| | | | |
|---|---|---|---|
| 3,598,126 A | * | 8/1971 | Hoeltzenbein .............. 604/526 |
| 3,734,083 A | | 5/1973 | Kolin ......................... 128/2.05 |
| 4,129,129 A | | 12/1978 | Amrine ....................... 128/214 |
| 4,350,161 A | | 9/1982 | Davis, Jr. .................... 128/349 |
| 4,362,163 A | * | 12/1982 | Krick ........................... 604/526 |
| 4,451,252 A | | 5/1984 | Martin ......................... 604/43 |
| 4,543,087 A | | 9/1985 | Sommercorn et al. ......... 604/43 |
| 4,545,374 A | | 10/1985 | Jacobson ..................... 128/303 |
| 4,589,868 A | | 5/1986 | Dretler ......................... 604/96 |
| 4,596,548 A | | 6/1986 | DeVries et al. ................ 604/4 |
| 4,619,643 A | * | 10/1986 | Bai .............................. 604/43 |

(Continued)

FOREIGN PATENT DOCUMENTS

EP        300 114        1/1988

(Continued)

OTHER PUBLICATIONS

Form PCT/ISA/210 International Search Report, PCT/US99/01368, date of mailing Jun. 10, 1999.

(Continued)

*Primary Examiner*—Phillip Gray
(74) *Attorney, Agent, or Firm*—Mike Jaro; Jeff Hohenshell

(57) ABSTRACT

A method of performing minimally invasive cardiac surgery includes the step of creating an access aperture into a patient's chest cavity, the access aperture being considerably smaller than a traditional cardiac surgery incision. A cannula is provided that has an oval portion with a longer major axis and a shorter minor axis and the cannula is inserted into the chest cavity through the access aperture.

26 Claims, 5 Drawing Sheets

U.S. PATENT DOCUMENTS

| | | | |
|---|---|---|---|
| 4,639,252 A | 1/1987 | Kelley et al. | 604/282 |
| 4,675,004 A | 6/1987 | Hadford et al. | 604/44 |
| 4,784,651 A | 11/1988 | Hickey | 604/282 |
| 4,795,439 A | 1/1989 | Guest | 604/43 |
| 4,804,359 A | 2/1989 | Grunwald et al. | 604/4 |
| 4,808,158 A | 2/1989 | Kreuzer et al. | 604/49 |
| 4,846,806 A | 7/1989 | Wigness et al. | 604/175 |
| 4,973,321 A | 11/1990 | Michelson | 604/280 |
| 5,045,075 A | 9/1991 | Ersek | 604/317 |
| 5,160,325 A | 11/1992 | Nichols et al. | 604/247 |
| 5,180,387 A | 1/1993 | Ghajar et al. | 604/266 |
| 5,201,712 A | 4/1993 | Bryant | 604/164 |
| 5,333,614 A | 8/1994 | Feiring | 128/662.06 |
| 5,348,536 A | 9/1994 | Young et al. | 604/43 |
| 5,374,245 A | 12/1994 | Mahurkar | 604/43 |
| 5,387,197 A | 2/1995 | Smith et al. | 604/164 |
| 5,395,330 A | 3/1995 | Marcadis et al. | 604/96 |
| 5,451,206 A | 9/1995 | Young | 604/43 |
| 5,536,251 A | 7/1996 | Evard et al. | 604/93 |
| 5,540,711 A | 7/1996 | Kieturakis et al. | 606/192 |
| 5,554,136 A | 9/1996 | Luther | 604/264 |
| 5,556,390 A | 9/1996 | Hicks | 604/280 |
| 5,569,182 A | 10/1996 | Twardowski et al. | 604/43 |
| 5,624,413 A * | 4/1997 | Markel et al. | 604/523 |
| 5,674,240 A | 10/1997 | Bonutti et al. | 606/198 |
| 5,682,906 A * | 11/1997 | Sterman et al. | 128/898 |
| 5,762,629 A | 6/1998 | Kambin | 604/164 |
| 5,799,661 A | 9/1998 | Boyd et al. | 128/898 |
| 5,817,071 A | 10/1998 | Dewindt et al. | 604/264 |
| 5,823,956 A | 10/1998 | Roth et al. | 600/374 |
| 5,830,191 A | 11/1998 | Hildwein et al. | 604/175 |
| 5,868,703 A * | 2/1999 | Bertolero et al. | 604/102.01 |
| 5,924,424 A | 7/1999 | Stevens et al. | 128/898 |
| 6,146,371 A | 11/2000 | DeWindt et al. | 604/506 |
| 6,447,484 B1 | 9/2002 | Briscoe et al. | 604/164.02 |
| 6,645,194 B2 * | 11/2003 | Briscoe et al. | 604/506 |

FOREIGN PATENT DOCUMENTS

GB  2172203  9/1986

OTHER PUBLICATIONS

Form PCT/ISA/210 International Search Report, PCT/US98/00361, date of mailing Jun. 12, 1998.

Arom et al.; Mini-Sternotomy for Coronary Artery Bypass Grafting; Ann. Thorac. Surg. 1996; 61: 1271-2.

Acuff et al.; Minimally Invasive Coronary Artery Bypass Grafting; Ann. Thorac. Surg. 1996; 61: 135-7.

Mathias; Keyhole Cardiac Surgery, MIS Techniques Could Transform Heart Surgery; OR Manager, Jul. 1996, vol. 12, No. 7.

* cited by examiner

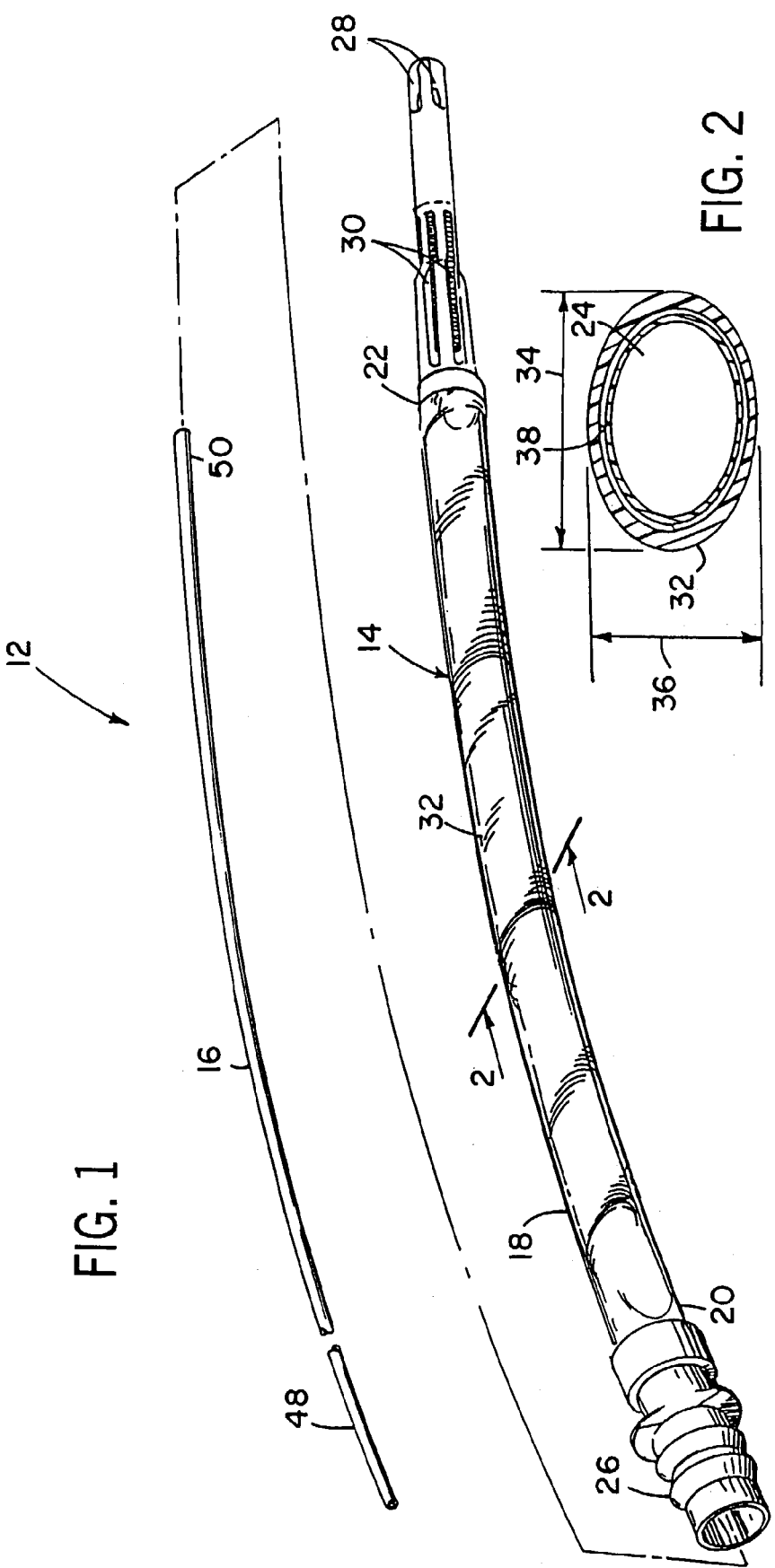

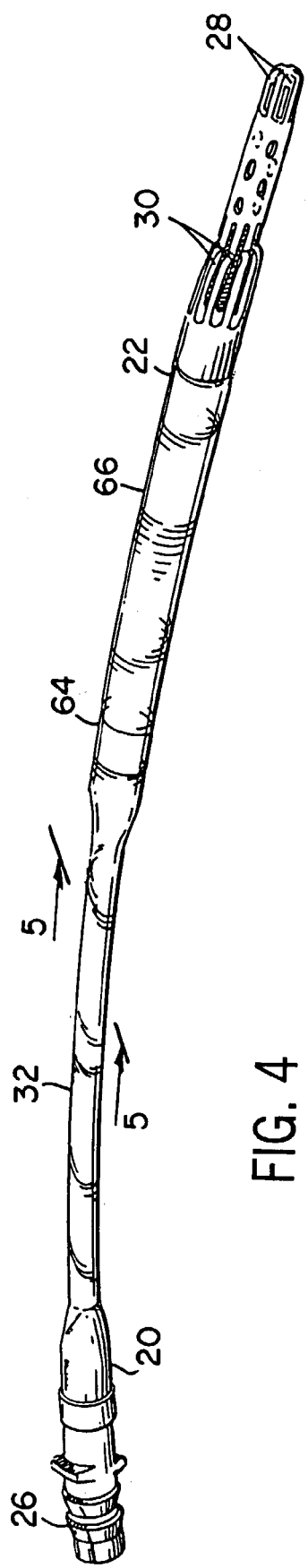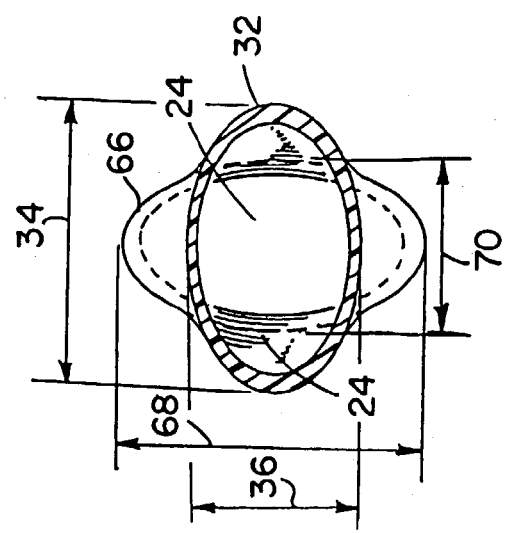
FIG. 4
FIG. 5

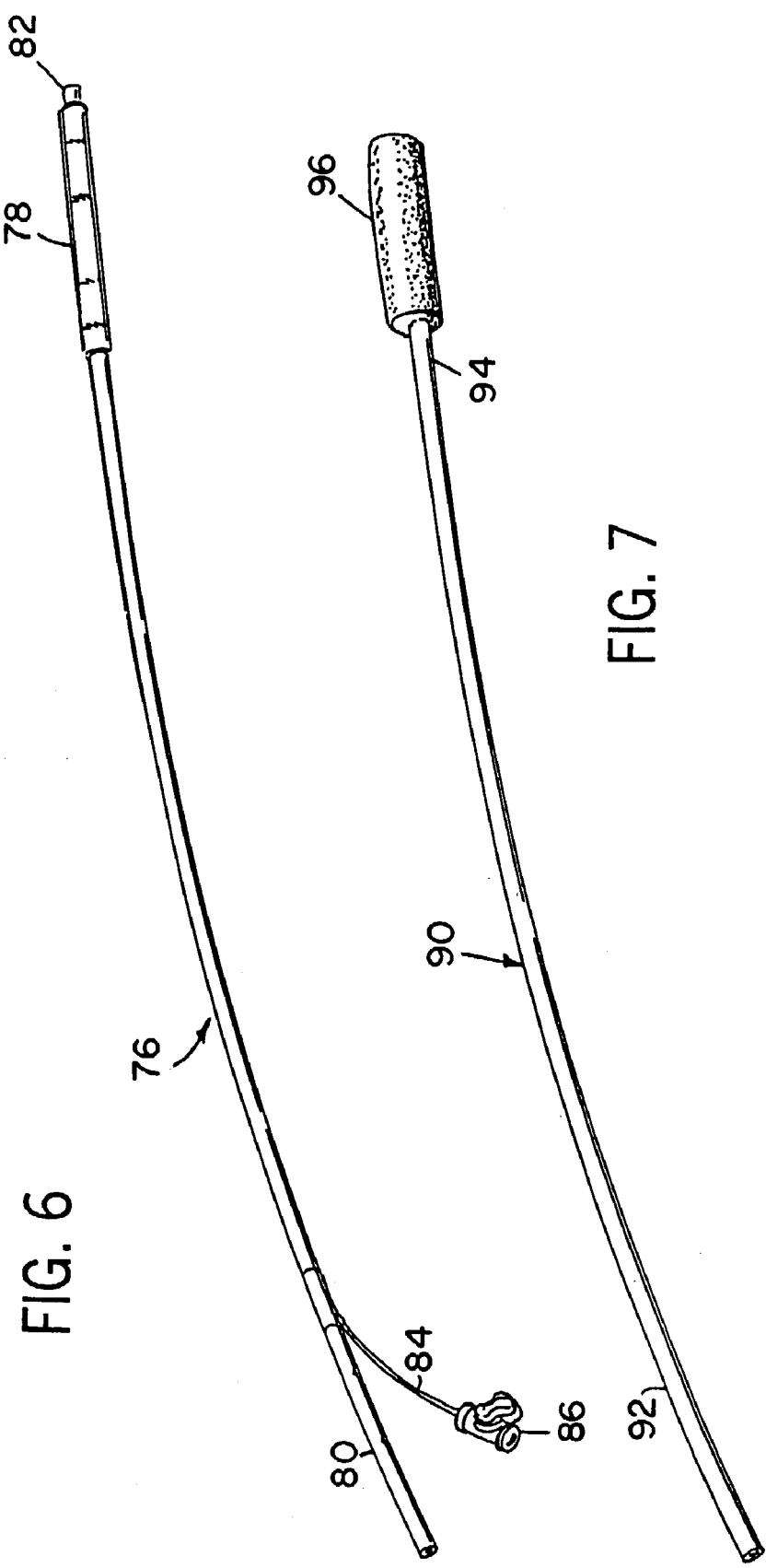

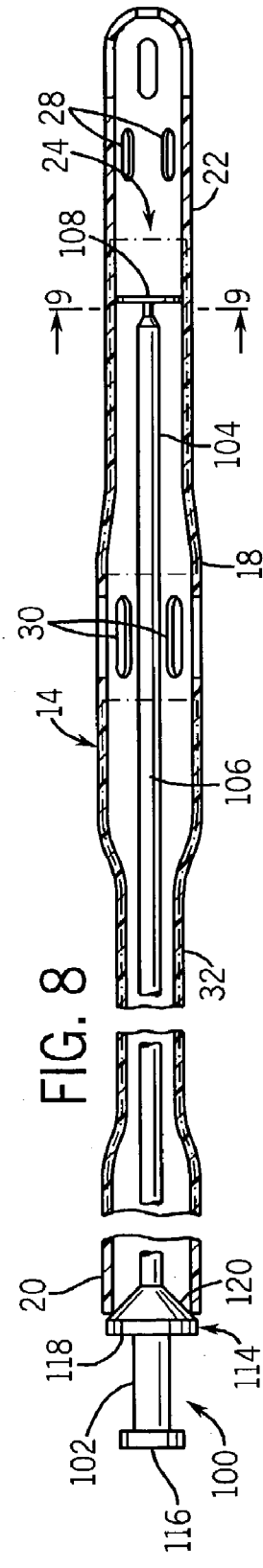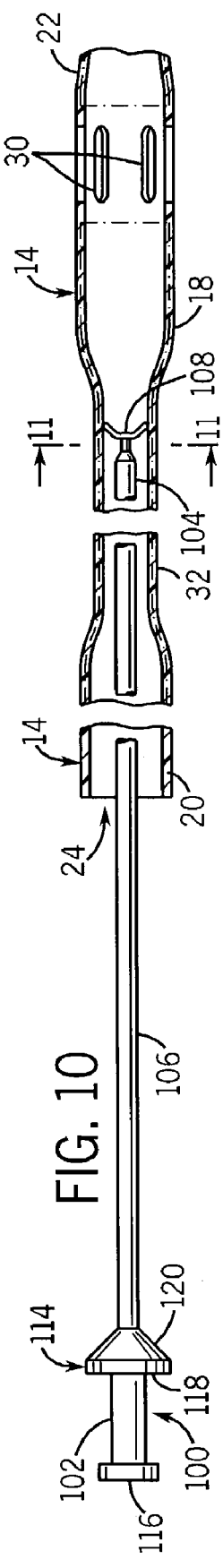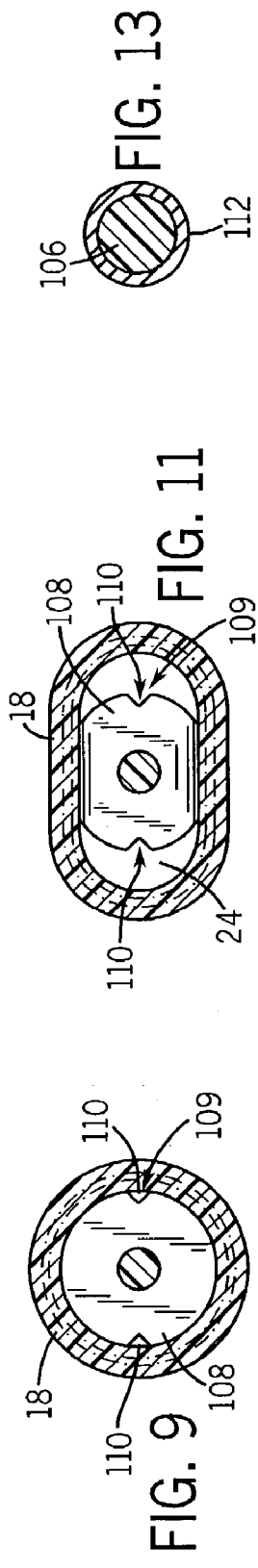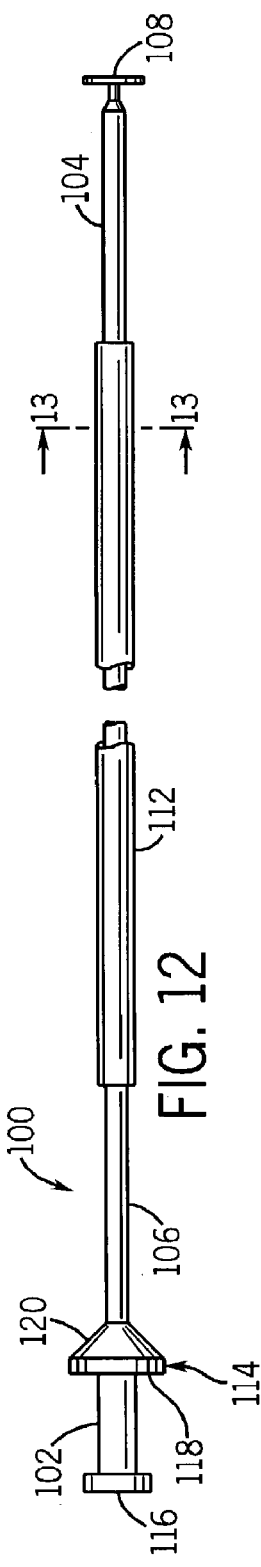

OVAL-SHAPED CARDIAC CANNULA

CROSS-REFERENCE TO RELATED PATENT APPLICATIONS

This application is a continuation of U.S. application Ser. No. 10/026,234, filed Dec. 21, 2001 now U.S. Pat. No. 6,645,194, which is a continuation of U.S. application Ser. No. 09/012,520 filed Jan. 23, 1998, U.S. Pat. No. 6,447,484, which is a continuation in part of U.S. application Ser. No. 08/780,995, filed Jan. 9, 1997, U.S. Pat. No. 5,817,071, all of which are incorporated herein by reference in their entirety.

BACKGROUND OF THE INVENTION

1. Field of the Invention

This invention relates to cannulas and, more particularly, to a cannula which is oval-shaped in cross-section and therefore ideally suited for use in minimally invasive surgical procedures.

2. Description of the Related Art

Cannulas have a wide variety of applications during surgical procedures. For example, in coronary surgery, venous and arterial cannulas are used to conduct blood between the body and bypass equipment. Cannulas are used to conduct cardioplegia solution for both antigrade and retrograde solution administration, and cannulas are also used as vents, sumps, and for chest tube fluid suction. The structure for these known cannulas generally comprises a cannula body which is circular in cross-section and has at least one lumen extending therethrough which is similarly circular in cross-section. Examples of these structures are seen in U.S. Pat. Nos. 4,639,252, 4,129,129 and 5,395,330.

A recent trend in surgical procedures is to minimize the size of the access apertures formed in the chest cavity. These procedures include mini-sternotomy and minimally invasive cardiac surgery. In each of these procedures, the goal is to reduce the size of the aperture in the chest wall. One problem in achieving this goal is the size, geometry, and space requirements for the instruments, cannulas, and the like which must pass through the reduced size apertures.

SUMMARY OF THE INVENTION

The cannula according to the invention overcomes the problems of the prior art by providing a cannula having a prescribed geometry, which more efficiently occupies the space of the aperture without adversely affecting the fluid rate therethrough.

The invention relates to a method of performing minimally invasive cardiac surgery. The method includes the steps of creating an access aperture into a patient's chest cavity that is considerably smaller than a median sternotomy, providing a cannula having an oval portion with a longer major axis and a shorter minor axis, and inserting the cannula into the chest cavity through the access aperture.

The invention further relates to a method of forming a venous cannula. The method includes the step of providing a length of tubing having an outer circular cross-section and having a helically wound wire supporting the tubing wall, the length of tubing having a proximal end and a distal end. The method further includes the steps of forming a segment in the length of tubing, the segment having an outer oval cross-section, such that the proximal end and the distal end of the length of tubing remain with an outer circular cross-section, and providing a flow aperture on the distal end of the length of tubing.

Further still, the invention relates to a cannula for use in conducting fluid to or from a body. The cannula includes a cannula body having a proximal end, a distal end, and a lumen extending between the proximal and distal ends, a first fluid aperture formed on the proximal end, and a second fluid aperture formed adjacent the distal end. A cross-section of a first portion of the cannula body is non-circular and has a major cross-sectional axis and a minor cross-sectional axis, the length of the major axis being greater than the length of the minor axis. The lumen extending through the first portion of the cannula body has the same cross-sectional shape as the cross-section of the first portion of the cannula body.

Other advantages of the invention will become apparent from the detailed description given hereinafter. It should be understood, however, that the detailed description and specific embodiments are given by way of illustration only, since, from this detailed description, various changes and modifications within the spirit and scope of the invention will become apparent to those skilled in the art.

BRIEF DESCRIPTION OF THE DRAWINGS

The invention will now be described with reference to the drawings in which:

FIG. 1 is a perspective view of a venous cannula assembly wherein at least a portion of the cannula body is oval in cross-section;

FIG. 2 is a cross-sectional view taken generally along the line 2-2 of FIG. 1 showing the oval cross-section of the cannula body;

FIG. 4 is a perspective view of a second embodiment of the cannula wherein at least two portions of the cannula body are oval in cross-section and the oval sections are not aligned with one another;

FIG. 5 is a cross-sectional view taken generally along the line 5-5 of FIG. 4 showing the oval cross-sections of the second embodiment of the cannula body;

FIG. 6 is a plan view of a second embodiment of the obturator for the cannula assembly;

FIG. 7 is a plan view of a third embodiment of the obturator;

FIG. 8 is a partial cross-sectional view of the cannula of FIG. 1 with a fourth embodiment of the obturator for the cannula assembly, showing the obturator fully inserted in the cannula;

FIG. 9 is a cross-sectional view taken generally along the line 9-9 of FIG. 8;

FIG. 10 is a partial cross-sectional view of the cannula of FIG. 1 showing the fourth embodiment of the obturator partially retracted;

FIG. 11 is a cross-sectional view taken generally along the line 11-11 of FIG. 10;

FIG. 12 is a plan view of the obturator shown in FIGS. 8-11 and including a malleable, stainless steel sleeve; and FIG. 13 is a cross-sectional view taken generally along the line 13-13 of FIG. 12.

DETAILED DESCRIPTION OF THE PREFERRED EMBODIMENTS

Figure 3:
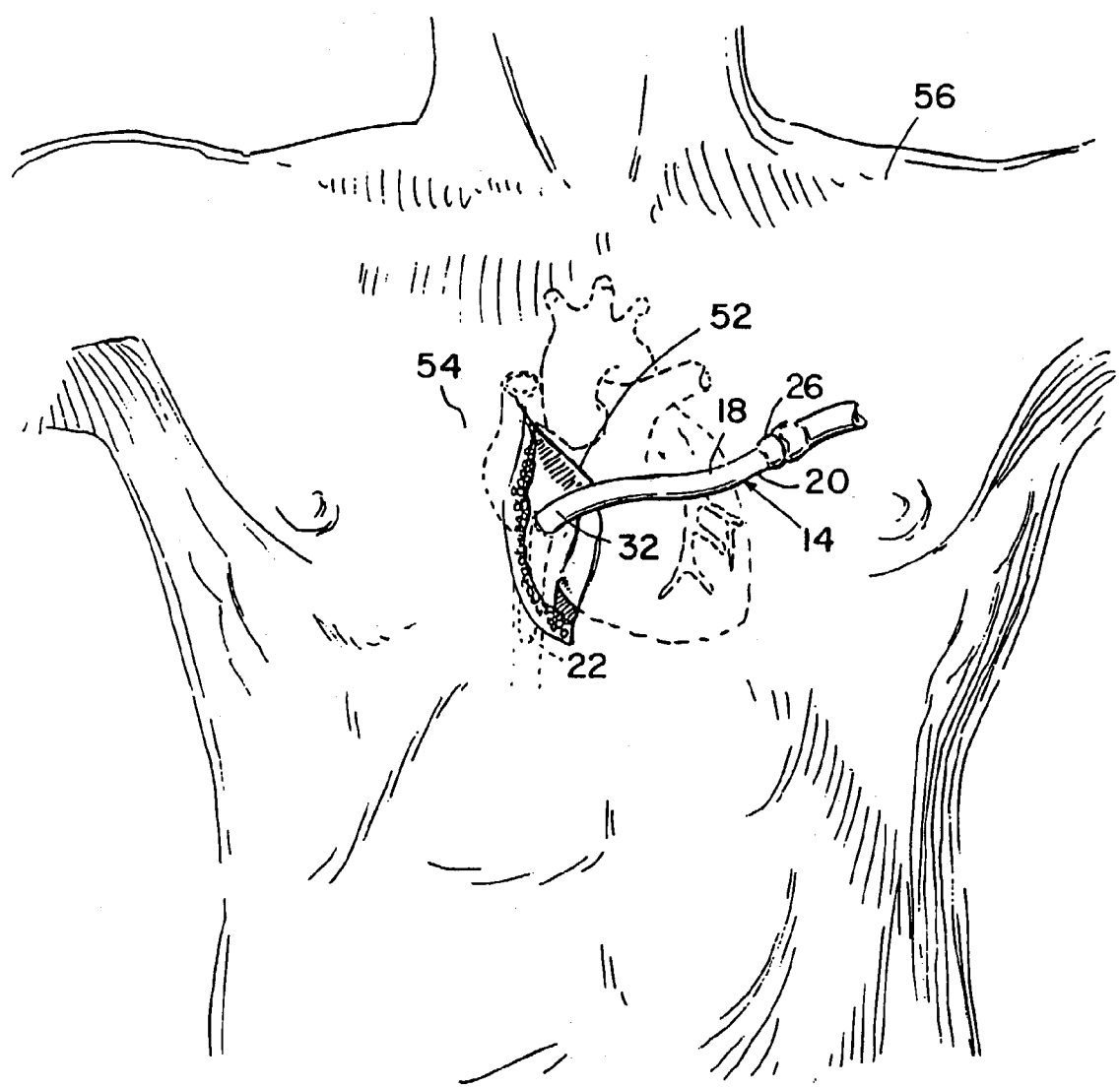
FIG. 3 is a plan view of a patient showing a cannula according to the invention passing through a mini-thoracotomy.

Turning now to the drawings and to FIGS. 1 and 2 in particular, a first embodiment of the cannula assembly according to invention is shown. The first embodiment of the cannula assembly 12 comprises a cannula 14 and an obturator 1 6 which is selectively, telescopically received in the cannula 14. The cannula 14 comprises a cannula body 18 having a proximal end 20, a distal end 22, and a lumen 24 extending between the proximal and distal ends. A conventional luer connector 26 is preferably provided on the proximal end 20, and the distal end 22 preferably includes at least one fluid inlet aperture for the receipt of fluid into the lumen. A helically wound reinforcing spring 38 is preferably, integrally formed into the cannula body 18. The cannula seen in FIGS. 1 and 2 includes a first set of fluid apertures 28 formed immediately adjacent the distal end 22 and a second set of apertures 30 formed a spaced distance proximally from the distal end. This structure is ideally suited for use as a venous cannula during a cardiac surgical procedure.

One unique feature of the cannula assembly according to the invention is that at least a portion of the cannula body 18 is non-circular. This first non-circular portion 32 is preferably oval in cross-section and is defined by a major cross-sectional axis 34 and a minor cross-sectional axis 36. As will be described further below, the incorporation of a non-circular portion 32 makes the cannula assembly according to the invention ideally suited for use in minimally invasive cardiac surgical procedures.

The obturator 16 comprises a proximal end 48 and a distal end 50. The obturator is adapted to be slidably, telescopically received inside the lumen 24 of the cannula 14. When the obturator is fully received inside the cannula lumen 24, the obturator substantially seals the second set of fluid apertures 30 so that fluid cannot enter the lumen 24 from the first set of fluid apertures 28 and then egress into the operation field through these apertures.

The cannula assembly 12 described above is ideally suited for use as a venous cannula during a coronary surgical procedure similar to the cannula described in U.S. Pat. No. 4,129,129 which is expressly incorporated herein by reference. In use, the cannula 14, with the obturator 16 fully received therein, is inserted through an appropriate incision into the right atrium and the inferior vena cava. As the distal end 22 of the cannula 14 is inserted into the blood flow passing through the right atrium and inferior vena cava, blood will enter the first set of fluid apertures 28, but the obturator 16 will restrict the flow of blood through the lumen 24 to the second set of fluid apertures 30. Once the cannula 14 is properly positioned, the obturator 16 is removed from the cannula 14, and the luer connector 26 of the cannula 14 is connected to a conventional bypass system. With the cannula 14 in this position, blood enters the lumen 24 through both the first and second fluid apertures 28, 30 and is conducted to the bypass machine.

Traditional cardiac surgery is typically performed by a median sternotomy in which substantially the entire chest cavity is exposed by cutting the full length of the sternum and spreading back the sternum and ribs to expose the entire pericardium. However, a recent trend in cardiac surgery is to attempt to minimize the size of the access apertures formed in the patient's chest using techniques such as a right or left anterior thoracotomy, mini-sternotomy, and multi-port access apertures. In each of these procedures, the size of the access aperture formed in the patient's chest is considerably smaller than the traditional median sternotomy, thereby reducing the complications and possible side effects associated with such a massive wound. However, reducing the size of the access aperture raises a new set of problems not encountered in the conventional median sternotomy, namely, sufficient space for the receipt of all the instruments and equipment.

One limiting factor to reducing the size of the access aperture in any surgical procedure is the cross-sectional space requirements of the surgical tools which must be inserted through the access aperture. The cannula according to the invention is an improvement over the known cannulas because it more efficiently utilizes the limited space of the access aperture without adversely affecting the fluid flow characteristics through the cannula.

As seen in FIGS. 1-3, at least a portion 32 of the cannula body 18 is oval in cross-section, and the cannula body 18 is received in an access aperture 52 formed in the chest wall 54 of the patient 56. In this example, the access aperture 52 comprises a right anterior thoracotomy. Preferably, the proximal 20 and distal 22 ends of the cannula 14 are circular in cross-section while the central portion of the cannula body 18 is oval in cross-section. When the oval portion 32 of the cannula is positioned in the access aperture 52, the available cross-sectional area of the access aperture 52 is used more efficiently. Preferably, the cannula is positioned so that the minor cross-sectional axis 36 extends radially inwardly from the sidewall of the access aperture 52. With this structure, the cannula 14 extends a minimum distance inwardly toward the center of the access aperture 52 thereby utilizing the available space more efficiently. If a traditional cannula having a round cross-section with a flow rate potential comparable to the oval-shaped cannula according to the invention were positioned in the access aperture 52, then the diameter of the round cannula would extend farther toward the center of the access aperture 52 and utilize the valuable cross-sectional area of the opening far more inefficiently.

While the preferred embodiment of the cannula 14 and cannula assembly 12 described above is a venous cannula, it is to be understood that the invention extends to any cannula inserted into the body through an access aperture including but not limited to an arterial cannula, a cardioplegia cannula (both retrograde and antigrade), a vent, a sump, or a suction tube. Similarly, FIG. 3 shows use of a cannula in a right anterior thoracotomy. It is to be understood that the benefits of the invention can be realized regardless of the particular surgical aperture which is created.

FIGS. 4 and 5 show a second embodiment of the cannula according to the invention. In this embodiment, the cannula 64 also includes a second non-circular portion 66. Preferably, the second non-circular portion is oval in cross-section and has a major cross-sectional axis 68 and a minor cross-sectional axis 70 with the major cross-sectional axes 34, 68, respectively, of the first and second non-circular portions 32, 66 not being parallel to one another and preferably perpendicular to one another. With this structure, the first non-circular portion 32 can be positioned to extend through the access aperture 52 as described above, and the second non-circular portion 66 can be positioned either inside the body or outside the body in a particular position which requires significant bending or deflection of the cannula 64.

A second embodiment of the obturator 76 is shown in FIG. 6. When the cannula is used as a venous cannula during a cardiac surgical operation, it is preferred to include an obturator which substantially seals the second set of fluid apertures 30 from the first set of fluid apertures 28 during the initial insertion of the cannula 14 in to the blood flow. In the preferred embodiment of the cannula 14, the minor cross-sectional axis 36 of the non-circular portion 32 is less than the interior diameter of the distal end 22 of the cannula 14. Therefore, in order for the obturator to be telescopically inserted and removed from the lumen, whatever means are incorporated onto the obturator must be pliable or radially expandable to accommodate these diametrical constraints. In this embodiment, an expandable member such as a conventional, silicone balloon 78 is provided on the distal end 50 of the obturator 76. The obturator 76 comprises a proximal end 80 and a distal end 82. The balloon 78 is fluidly connected to an inflation lumen 84 which extends from the balloon 78, to the proximal end of the obturator. Preferably, a luer connector 86 is mounted to the terminal end of the inflation lumen 84.

The balloon is adapted for inflation from a retracted state as seen in FIG. 6 to an expanded state which extends radially outwardly from the obturator 76 a sufficient distance to substantially seal the second set of fluid apertures 30. In use, the obturator 76 is inserted into the lumen 24 with the balloon 78 in the retracted state. Once the distal end 82 of the obturator 76 is received in the lumen 24 so that the balloon 78 is positioned immediately adjacent the second set of fluid apertures 30, the balloon 78 is inflated through the flow of pressurized fluid through the inflation lumen 84 and connector 86. The balloon 78 is inflated a sufficient amount to substantially seal the fluid apertures 30. Once the cannula assembly 12 is properly positioned in the blood flow, the balloon 78 is deflated by removing the pressurized fluid from the balloon 78 through the inflation lumen 84 and connector 86. Once the balloon 78 is sufficiently deflated, then the obturator 76 is removed from the cannula lumen 24, and the lumen is fluidly connected to the bypass system.

A third embodiment of the obturator 90 is shown in FIG. 7. Similar to the earlier embodiments, this embodiment of the obturator 90 comprises a proximal end 92 and a distal end 94. However, in this embodiment, an expandable foam member 96 is mounted on the distal end 94 of the obturator 90. In the relaxed state, the diameter of the foam member 96 is slightly larger than the interior diameter of the cannula 14 at the second set of fluid apertures 30. Therefore, when the foam member 96 is positioned immediately adjacent the apertures 30, the foam member will substantially seal the apertures 30 from the lumen 24.

In the third embodiment, the foam member 96 is formed from a soft, pliable foam which can easily be compressed by the opposed sidewalls of the cannula in the non-circular portion as the obturator 90 passes therethrough. Once the obturator 90 is fully received in the lumen 24, the foam member 96 expands outwardly a sufficient distance to substantially seal the fluid apertures 30. Similar to the earlier embodiments, once the cannula assembly 12 is properly positioned, then the obturator is telescopically removed from the lumen. As the obturator is being pulled through the non-circular portions, the opposed sidewalls of the lumen will compress the foam member a sufficient distance to permit passage of the foam member therethrough.

A fourth embodiment of the obturator 100 for a cannula 14 is shown generally in FIGS. 8-13. As with the earlier embodiments, the obturator 100 has a proximal end 102 and a distal end 104. The obturator 100 includes an elongate member 106 and a flexible disc 108, which is coupled to the distal end 104 of the elongate member 106. The flexible disc 108 is preferably, but not necessarily, thin. In the present embodiment of the invention, the flexible disc 108 is round and has a diameter substantially equal to the diameter of the lumen 24 at the distal end 22 of the cannula body 18. However, it should be noted that the flexible disc 108 may have a non-circular shape, provided that its shape corresponds to that of the lumen 24 at the distal end 22. As illustrated in FIG. 9, when the obturator 100 is fully inserted into the cannula lumen 24, the flexible disc 108 substantially seals the distal end of the lumen 24 to prevent the flow of blood, which enters through the first set of fluid apertures 28, from passing through the lumen 24 to the second set of fluid apertures 30. After the cannula 14 is inserted into a blood vessel, the obturator 100 is removed, allowing blood to flow through the first and second sets of fluid apertures 28 and 30, respectively, and into the lumen 24.

The flexible disc 108 is formed from a durable material which is sufficiently flexible that the edges of the disc 108 bend, enabling the disc 108 to pass through the first non-circular portion 32 of the cannula body 18, as shown in FIG. 10, and is also sufficiently stiff to occlude the distal end 22 of the lumen 24 when the cannula 14, with the obturator 100 inserted therein, is positioned in a body. The flexible disc 108 is preferably made of polypropylene or polyethylene but may also be made of other materials, such as foam, teflon, or other plastics.

As shown in FIGS. 9 and 11, the flexible disc 108 further includes a feature 109 for allowing air to escape from the proximal end 20 of the cannula 14. Preferably, the feature 109 is at least one tiny notch 110 formed in the flexible disc 108. The present obturator 100 has two notches 110 located along the edge of the flexible disc 108 and diametrically opposed from each other. However, any number of notches may be provided on the flexible disc 108. The feature 109 may also be apertures (not shown) formed in an interior region of the disc 108, rather than notches disposed along the edge. The notches 110 prevent air in the distal end 22 of cannula 14 from being introduced into a vein or artery, when the cannula 14 is inserted therein. The notches 110 are sufficiently small to enable air in the distal end 22 of the cannula lumen 24 to escape out the proximal end 20, while preventing blood from doing the same. As the cannula 14 is inserted into a chamber of the heart or vessel, pressure from blood entering the first set of fluid apertures 28 forces any air trapped in the distal end 22 of the cannula lumen 24 through the notches 11 0, enabling air to escape out the proximal end 20 of the cannula 14.

The elongate member 106 of the obturator 100 may be a solid shaft or wire, or a hollow tube. It is preferred that the elongate member 106 and flexible disc 108 are integrally formed as a single piece, such as by injection molding. However, the elongate member 106 and flexible disc 108 may also be separate and distinct pieces, that are coupled together in a conventional manner.

As shown in FIGS. 12 and 13, the obturator 100 may include a sleeve 112 that is injection molded directly therein. The sleeve 112, which is preferably made of a malleable material, such as stainless steel, wraps around the exterior of the elongate member 106 and extends along at least a portion of the length thereof. Since the sleeve 112 is made of a malleable material, the cannula 14, with the obturator 100 in place, may be bent to a desired configuration, prior to insertion in the body, and will maintain that configuration. In lieu of the sleeve 112, a malleable wire or rod (not shown), disposed inside the elongate member 106, will also provide such a pliable structure.

The obturator 100 preferably further includes a stop 114 and a collar or grip 116 as shown. The stop 114 is located on the elongate member 106, adjacent the proximal end 102, and limits the depth of insertion of the obturator 100 in the cannula lumen 24 to prevent damage to either the flexible disc 108 or the distal end 22 of the cannula 14. In the preferred embodiment of the obturator 100, the stop 114 is conical in shape and includes a flat surface 118 and an inclined surface 120. It should be noted, however, that other configurations for the stop 114 may be envisioned. The inclined surface 120 of the conical stop 114 extends toward the distal end 104 of the elongate member 106, while the flat surface 118 is located proximally of the inclined surface 120. When the obturator 100 is fully inserted in the cannula 14, the stop 114 abuts the proximal end 20 of the cannula 14, with a portion of the inclined surface 120 being received in the cannula lumen 24.

The grip 116 is provided at the proximal end 102 of the obturator 100 and is coupled to the elongate member 106. The grip 116 extends beyond the diameter of the elongate member 106 and enables a user to grasp the obturator 100 and remove it from the cannula 14. The grip 116, stop 114, elongate member 106 and flexible disc 108 of the obturator 100 are preferably injection molded as a single, integral piece. However, as discussed above, two or more pieces of the obturator 100 may be separate and distinct and may be coupled together in a conventional manner.

The flexible disc 108 of the obturator 100, the foam member 96 of the obturator 90, and the expandable balloon 78 of the obturator 76 are only three examples of expandable means provided on the obturator to permit passage of the distal end of the obturator through the confines of the lumen and still capable of restricting the flow of fluid through the lumen of the catheter. It is understood that any other means which accommodate the varying diameters fall within the scope of the invention.

The preferred method for forming the cannula 14 according to the invention comprises the steps of extruding a circular length of tubing. Preferably, tubing is formed from silicone or polyvinyl chloride. Depending upon the particular application, a helically wound spring may be received on the inside of the hollow tube and either be adhesively fastened therein or integrally molded therein. Next, the tubing is cut to the desired length, and then the non-circular portion is formed by positioning the length of the tube between two opposed platens and then compressing the two platens a sufficient distance to obtain the desired non-circular or oval-shaped configuration. Once the spring has been plastically deformed, it will retain the pliable cannula body in the oval or non-circular configuration. Finally, the luer connector and flow aperture member are mounted to the proximal and distal ends thereof. The cannula 14 can be compressed to create the non-circular configuration prior to or subsequent to mounting of the elements on the proximal and distal ends thereof. In the event that two different non-circular portions are formed along the length of the cannula, then the step of compressing the cannula body between two opposed platens is repeated, as necessary, for the additional non-circular sections.

With the rapid evolution of surgical procedures which minimize the size of the access aperture cut into the patient, the known, conventional, surgical tools such as cannulas, vents, sumps, or suction tubes must be adapted to accommodate such advances. The non-circular cannula according to the invention is one such modification which assists the surgeons in achieving the goal of minimizing the wound size for a variety of surgical procedures. This advantage is accomplished without adversely affecting the fluid flow rate through the tubing or otherwise adversely affecting the performance of the tubing.

Reasonable variation and modification are possible within the spirit of the foregoing specification and drawings without departing from the scope of the invention.

What is claimed is:

1. A method of performing minimally invasive cardiac surgery, comprising the steps of:
   creating an access aperture into a patient's chest cavity, wherein the access aperture is considerably smaller than a median sternotomy;
   providing a cannula having a first oval portion with a longer major axis and a shorter minor axis and a second oval portion with a longer major axis and a shorter minor axis, the longer major axis of the first oval portion being oriented substantially perpendicular to the longer major axis of the second oval portion;
   inserting the cannula into the chest cavity through the access aperture, wherein the first oval portion is positioned to extend through the access aperture;
   providing an obturator received within the cannula; and
   removing the obturator from the cannula.

2. The method of claim 1, wherein creating the access aperture does not require cutting a patient's sternum.

3. The method of claim 1, wherein the cannula is a venous cannula.

4. The method of claim 1, wherein a helically wound reinforcing device is integrated into the cannula.

5. The method of claim 1, wherein the cannula is a cardioplegia cannula.

6. The method of claim 1, wherein the access aperture is an anterior thoracotomy.

7. The method of claim 1, wherein the access aperture is a mini-sternotomy.

8. The method of claim 1, further comprising the step of positioning the cannula such that the minor axis extends radially inward from a side wall of the access aperture.

9. The method of claim 1, further comprising the step of connecting the cannula to a conventional heart bypass system.

10. A method of performing minimally invasive cardiac surgery, comprising the steps of:
    creating an access aperture into a chest cavity, wherein the access aperture is considerably smaller than a median sternotomy;
    providing a cannula having a first oval portion with a longer major axis and a shorter minor axis and a second oval portion with a longer major axis and a shorter minor axis, the longer major axis of the first oval portion being oriented substantially perpendicular to the longer major axis of the second oval portion;
    inserting the cannula into the chest cavity through the access aperture, wherein the first oval portion is positioned to extend through the access aperture; performing a surgical procedure on the heart;
    providing an obturator received within the cannula; and
    removing the obturator from the cannula.

11. The method of claim 10, wherein the surgical procedure comprises the step of creating multiple access ports in the patient's chest cavity.

12. The method of claim 10, wherein the entire length of the cannula is oval.

13. The method of claim 10, further comprising the step of conducting blood with the cannula.

14. The method of claim 13, wherein the blood is delivered to a heart bypass system.

15. The method of claim 10, wherein creating the access aperture does not require cutting a patient's sternum.

16. The method of claim 15, wherein the cannula is a venous cannula.

17. The method of claim 10, wherein a helically wound reinforcing device is integrated into the cannula.

18. The method of claim 10, wherein the cannula is a cardioplegia cannula.

19. The method of claim 10, wherein the access aperture is an anterior thoracotomy.

20. The method of claim 10, wherein the access aperture is a mini-sternotomy.

21. The method of claim 10, further comprising the step of positioning the cannula such that the minor axis extends radially inward from a side wall of the access aperture.

22. The method of claim 10, further comprising the step of connecting the cannula to a heart bypass system.

23. A method of efficiently utilizing the area of a percutaneous aperture during cardiac surgery, comprising the steps of:
    providing a cannula having a helically wound reinforcing member, a proximal circular cross-sectional segment, an intermediate oval cross-sectional segment having a longer major axis and a shorter minor axis, and a distal circular cross-sectional segment having a flow inlet;
    inserting the distal segment into a chest cavity through the aperture; and
    positioning the cannula such that the intermediate oval cross-sectional segment extends through the aperture with the minor axis extending inwardly from a side wall of the aperture, thereby efficiently utilizing the area of the aperture.

24. The method of claim 23, further comprising the step of connecting a leur connector to the proximal segment.

25. The method of claim 23, further comprising the step of connecting the cannula to a heart bypass system.

26. A cannula for use in conducting fluid to or from a body, comprising:
    a cannula body having a proximal end, a distal end, and a lumen extending between the proximal and distal ends;
    a first fluid aperture formed on the proximal end; and
    a second fluid aperture formed adjacent the distal end;
    wherein a cross section of a first portion of the cannula body is non-circular and has a major cross-sectional axis and a minor cross-sectional axis, the length of the major axis being greater than the length of the minor axis and wherein the lumen extending through the first portion of the cannula body has the same cross-sectional shape as the cross section of the first portion of the cannula body.

* * * * *